US010631816B2

(12) United States Patent
Fackelmeier et al.

(10) Patent No.: US 10,631,816 B2
(45) Date of Patent: Apr. 28, 2020

(54) TRANSMISSION SYSTEM FOR THE CONTACTLESS TRANSMISSION OF AN ELECTRICAL AND/OR ELECTROMAGNETIC SIGNAL

(71) Applicant: Siemens Healthcare GmbH, Erlangen (DE)

(72) Inventors: Andreas Fackelmeier, Thalmaessing (DE); Sebastian Martius, Forchheim (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 428 days.

(21) Appl. No.: 15/586,331

(22) Filed: May 4, 2017

(65) Prior Publication Data

US 2017/0332991 A1    Nov. 23, 2017

(30) Foreign Application Priority Data

May 18, 2016 (DE) .......................... 10 2016 208 539

(51) Int. Cl.
*A61B 6/00* (2006.01)
*H02J 50/10* (2016.01)
*A61B 6/03* (2006.01)

(52) U.S. Cl.
CPC .............. *A61B 6/56* (2013.01); *A61B 6/032* (2013.01); *H02J 50/10* (2016.02)

(58) Field of Classification Search
CPC .. A61B 6/032; A61B 6/56; H02J 50/05; H02J 50/10
See application file for complete search history.

(56) References Cited

U.S. PATENT DOCUMENTS

| 4,646,086 A | * | 2/1987 | Helzel ...................... A61B 6/56 340/870.29 |
| 5,530,424 A | | 6/1996 | Harrison et al. |

(Continued)

FOREIGN PATENT DOCUMENTS

| CN | 1130836 A | 9/1996 |
| CN | 1500221 A | 5/2004 |

(Continued)

OTHER PUBLICATIONS

Chinese Office Action and English translation thereof dated Jun. 26, 2019.

(Continued)

*Primary Examiner* — Chih-Cheng Kao
(74) *Attorney, Agent, or Firm* — Harness, Dickey & Pierce, P.L.C.

(57) ABSTRACT

A transmission system is disclosed for the contactless transmission of at least one electrical and/or electromagnetic signal from a first device part of a data-generating device to a second device part of the device by way of electrical and/or electromagnetic coupling. The first device part is set up to perform a movement relative to the second device part during operation. The transmission system includes a first transmission unit and a second transmission unit, either being arrangable on the first device part and the other being arrangable on the second device part. The first transmission unit includes a first coupler and a first auxiliary coupler and the second transmission unit includes a second coupler. For the electrical and/or electromagnetic coupling, the coupling strengths between the first coupler and the second coupler and between the first auxiliary coupler and the second coupler have different functional distance dependences.

22 Claims, 3 Drawing Sheets

(56) References Cited

U.S. PATENT DOCUMENTS

| | | |
|---|---|---|
| 2003/0185505 A1 | 10/2003 | Fink |
| 2006/0274853 A1* | 12/2006 | Schilling .............. A61B 6/56 375/295 |
| 2007/0040635 A1 | 2/2007 | Popescu et al. |
| 2007/0063785 A1 | 3/2007 | Krumme et al. |
| 2007/0198045 A1 | 8/2007 | Morton et al. |
| 2009/0185658 A1 | 7/2009 | Katcha et al. |
| 2009/0304144 A1 | 12/2009 | Beyerlein et al. |
| 2010/0310039 A1* | 12/2010 | Lindorfer .............. A61B 6/56 378/15 |
| 2011/0009078 A1 | 1/2011 | Kawamura |
| 2012/0082288 A1 | 4/2012 | Friesner et al. |
| 2013/0279647 A1* | 10/2013 | Krupica ............. G01N 23/046 378/19 |
| 2014/0227986 A1 | 8/2014 | Kanno |
| 2015/0038791 A1 | 2/2015 | Reichel |
| 2016/0143610 A1 | 5/2016 | Luthardt et al. |

FOREIGN PATENT DOCUMENTS

| | | |
|---|---|---|
| CN | 1935088 A | 3/2007 |
| CN | 1950740 A | 4/2007 |
| CN | 1989905 A | 7/2007 |
| CN | 101039621 A | 9/2007 |
| CN | 101339890 A | 1/2009 |
| CN | 101552123 A | 10/2009 |
| CN | 101958733 A | 1/2011 |
| CN | 102551775 A | 7/2012 |
| CN | 103765443 A | 4/2014 |
| CN | 104346912 A | 2/2015 |
| CN | 105615910 A | 6/2016 |
| CN | 105679005 A | 6/2016 |
| DE | 102004031355 A1 | 10/2005 |
| DE | 102008038362 A1 | 2/2010 |
| JP | 2001067449 A | 3/2001 |

OTHER PUBLICATIONS

Yeh, C. et al.: "The Essence of Dielectric Waveguides", California Advanced Studies, Los Angeles, USA, Springer US (2008), pp. 1-522, ISBN 978-0-387-30929-3.

German Office Action dated Jan. 9, 2017.

* cited by examiner

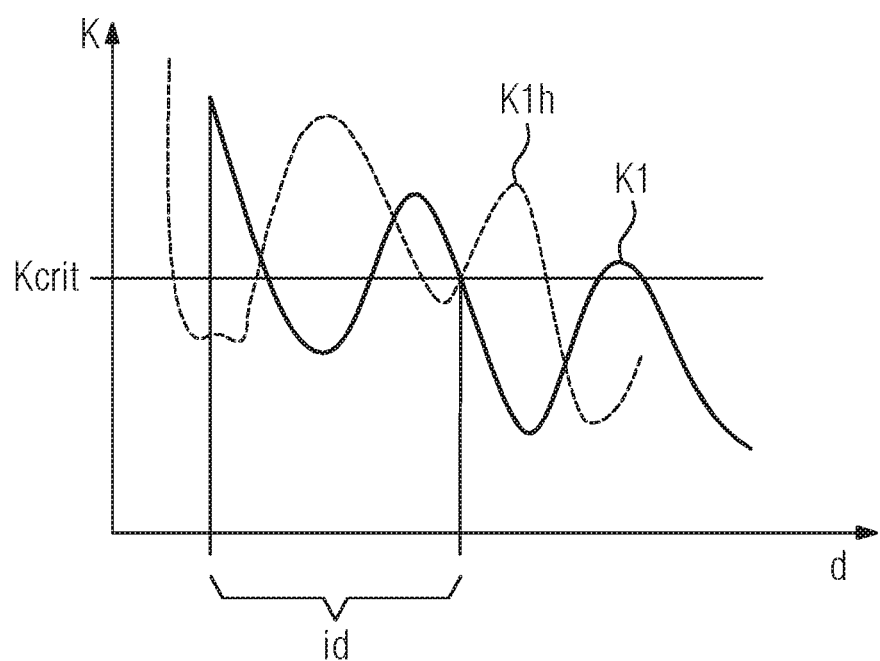

TRANSMISSION SYSTEM FOR THE CONTACTLESS TRANSMISSION OF AN ELECTRICAL AND/OR ELECTROMAGNETIC SIGNAL

PRIORITY STATEMENT

The present application hereby claims priority under 35 U.S.C. § 119 to German patent application number DE 102016208539.5 filed May 18, 2016, the entire contents of which are hereby incorporated herein by reference.

FIELD

At least one embodiment of the invention generally relates to a transmission system for the contactless transmission of at least one electrical and/or electromagnetic signal from a first device part of a data-generating device to a second device part of the device by way of electrical and/or electromagnetic coupling, wherein the first device part is set up to perform a movement relative to the second device part during operation of the device, wherein the transmission system comprises a first transmission unit and a second transmission unit, and wherein either the first transmission unit or the second transmission unit can be arranged on the first device part and the other transmission unit in each case can be arranged on the second device part. At least one embodiment of the invention further generally relates to a data-generating device correspondingly equipped with a transmission system, and a method for the transmission of an electrical and/or electromagnetic signal.

BACKGROUND

In a computed tomography device (CT), the data transmission between the permanently fixed mounting frame and the rotating assembly ("gantry") rotating relative thereto assumes an important role. On the one hand the individual items of image data generated are to be transmitted from the gantry to the mounting frame, in order to be able to forward them from there to the central image processing facility, and ultimately to provide the medical personnel with a sufficiently meaningful overall image. On the other hand data, in particular control data, is frequently also to be transmitted from the mounting frame to the rotating assembly during ongoing operation.

In a CT, data transmission between the gantry and the mounting frame frequently takes place via slip rings. As a result of the direct physical contact which is created for the transmission between a ring on the gantry and the sliding contacts on the mounting frame, these display an inherent abrasion, which over the course of long-term operation can impair the stability of the transmission, and may thus have to be compensated for. In addition the friction is increased by the physical contact, so that an increased energy demand for the rotation itself may arise, which is generally unwelcome.

The ever-increasing data volumes resulting from the higher resolution in the case of the imaging, and the requirements arising in terms of the data rate for the transmission pose a problem which has yet to be solved. One approach is to improve the data rates through the use of directional couplers, which are based on dielectric waveguides. The transmission here takes place essentially through the electromagnetic, in particular optical coupling-in of a signal, which is guided to the gantry by way of a dielectric waveguide, across the air gap into a further dielectric waveguide on the mounting frame.

SUMMARY

The inventors have recognized that a serious problem here is a difficult-to-control axially and radially variable offset of the mounting frame to the gantry during the operation of the CT as a result of the rotation of the gantry. As a result of this varying offset, the distance of the two dielectric waveguides, which form the major components of the directional coupler, is not constant. Seen from the respective level of the two waveguides, a distance variation of this kind has a normal and a longitudinal component, wherein the variation in the longitudinal component has significant effects on the coupling strength, that is on the signal strength received. The coupling strength here shows a complex functional interrelationship between the distance of the two waveguides from each other and their respective geometrical parameters (primarily: coupling length and cross section). No adequate solution for the problem is yet known.

The inventors have further recognized that the problem cited is, however, not limited solely to the area of medical tomography devices, but is of general relevance, if in a device with two device parts, which perform a movement relative to each other during operation of the device, data or also energy are to be transmitted from one device part to the other, and this would not, or not sensibly, be achievable by way of a cable connection because of the relative movement.

At least one embodiment of the invention therefore provides a transmission system for a data-generating device with two device parts, configured to perform a movement relative to each other during operation of the device which, with the simplest possible structure, should permit the most stable and reliable possible transmission of data and/or energy between the first device part and the second device part of the device.

According to at least one embodiment of the invention, this is achieved by way of a transmission system for the contactless transmission of at least one of an electrical and electromagnetic signal from a first device part of a data-generating device to a second device part of the device via at least one of electrical and electromagnetic coupling, wherein the first device part is set up to perform movement relative to the second device part during operation of the device, the transmission system comprising:

a first transmission unit including a first coupler and a first auxiliary coupler, differently dimensioned from the first coupler; and a second transmission unit including a second coupler, either the first transmission unit or the second transmission unit being arranged on the first device part and the other of the first or the second transmission unit being arranged on the second device part, wherein the respective coupling strengths between the first coupler and the second coupler and between the first auxiliary coupler and the second coupler, for the at least one of electrical and electromagnetic coupling, have respectively different functional distance dependences.

Advantageous and in part per se inventive embodiments are the subject of the claims and the following description.

At least one embodiment of the invention further specifies a data-generating device which comprises a first device part, a second device part and a transmission system of the previously described type, wherein the first device part is set up to perform a movement relative to the second device part during operation of the device, and wherein either the first transmission unit or the second transmission unit of the transmission system is arranged on the first device part, and the other transmission unit of the transmission system in each case is arranged on the second device part. The advantages specified for the transmission system and for its developments can be transferred analogously to the data-generating device.

In a further advantageous embodiment of the invention, the data-generating device is embodied as a computed tomography device, wherein the first device part is formed by the rotating assembly (gantry) and the second device part is formed by the mounting frame. In the case of computed tomography in particular a substantial amount of image data is generated in a short time as a result of the X-ray exposures, which is to be forwarded directly to the medical image processing facility for the purposes of the application. Because of the high rotational speed of the gantry a contactless transmission should preferably be selected here. The proposed embodiment with the transmission system described, whose first transmission unit has a first coupler and a first auxiliary coupler, is here particularly suitable to transmit image data of ever higher resolution from the gantry to the mounting frame.

At least one embodiment of the invention further specifies a method for the transmission at least of an electrical and/or electromagnetic signal from a first device part of a data-generating device to a second device part of the device, wherein the first device part performs a relative movement with reference to the second device part, and wherein an electrical and/or electromagnetic coupling is created at least temporarily between a first coupler arranged on the first device part and second coupler arranged on the second device part and a first auxiliary coupler arranged on the first device part and the second coupler in each case, or an electrical and/or electromagnetic coupling is created at least temporarily between a first coupler arranged on the second device part and a second coupler arranged on the first device part and a first auxiliary coupler arranged on the second device part and the second coupler in each case. It is here provided for the electrical and/or electromagnetic signal to be transmitted in a first signal transmission phase via the coupling between the first coupler and the second coupler, and to be transmitted in a second signal transmission phase via the coupling between the first auxiliary coupler and the second coupler.

Parts and variables which correspond to one another are provided with the same reference numerals in all the figures.

BRIEF DESCRIPTION OF THE DRAWINGS

An example embodiment of the invention is explained in greater detail below on the basis of a drawing. Here, represented in each case in schematic form:

FIG. 3 shows, in a functional diagram, the distance dependence of the coupling strengths in the transmission system according to FIG. 2.

DETAILED DESCRIPTION OF THE EXAMPLE EMBODIMENTS

Figure 1:
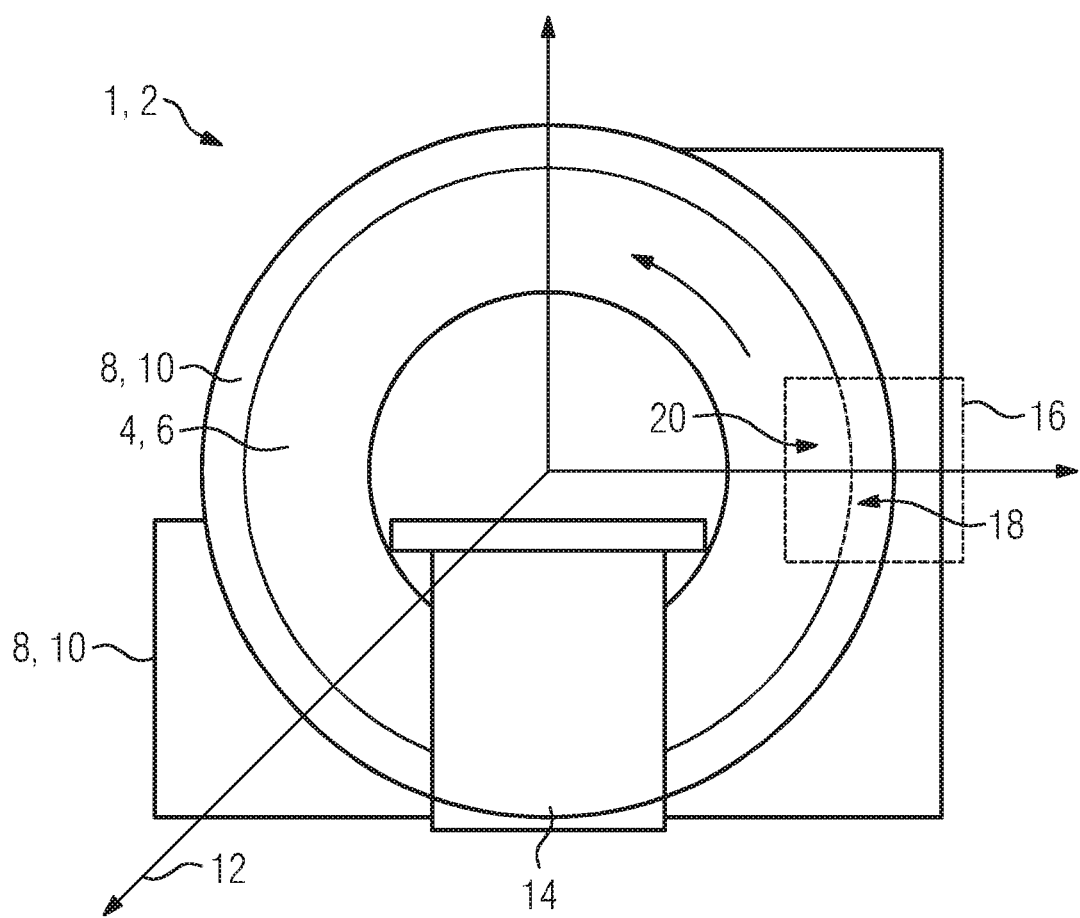
FIG. 1 shows, in a cross-sectional representation, a computed tomography device with a transmission system for the transmission of the image data.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

According to at least one embodiment of the invention this is achieved by way of a transmission system for the contactless transmission at least of an electrical and/or electromagnetic signal from a first device part of a data-generating device to a second device part of the device by way of electrical and/or electromagnetic coupling, wherein the first device part is set up to perform a movement relative to the second device part during operation of the device, wherein the transmission system comprises a first transmission unit and a second transmission unit, wherein either the first transmission unit or the second transmission unit can be arranged on the first device part and the other transmission unit in each case can be arranged on the second device part, wherein the first transmission unit has a first coupler and a first auxiliary coupler differently dimensioned from the first coupler, wherein the second transmission unit has a second coupler, and wherein for the electrical and/or electromagnetic coupling the coupling strengths between the first coupler and the second coupler and between the first auxiliary coupler and the second coupler in each case have different functional distance dependences. Advantageous and in part per se inventive embodiments are the subject of the subclaims and the following description.

A data-generating device should be taken to mean a device in which an electronic generation of data takes place. The generation of the data in particular takes place by way of a physical measuring and/or interaction process of or with the environment of the device. The measuring or interaction here preferably takes place via the first device part and a further data processing on the second device part. A relative movement of the first device part with reference to the second device part should be taken to mean that during operation of the data-generating device the second device part remains fixed in relation to its environment as intended, while the first device part moves relative to the second device part and thus in the same way also moves in relation to the environment.

The term transmission system should here encompass an apparatus which includes at least two parts, wherein at least one part of the apparatus is to be arranged on the first device part and on the second device part in each case, and which is set up to permit a transmission of the data from the first device part to the second device part via a physical process.

An electrical and/or electromagnetic coupling encompasses every coupling which is essentially based on electrical and/or electromagnetic processes, that is in particular a capacitive coupling and an optical directional coupling. To this effect a coupler is an apparatus which is set up to establish a connection for the transmission of a signal to a further, physically similar coupler, via a coupling of the specified type, that is for example two spatially separated electrodes for the transmission of a signal by way of a capacitive coupling between the electrodes with a sufficiently small distance. In this connection, coupling strength should be taken to mean in particular the physical interaction between two couplers which is the basis of the intensity of the coupling, which in turn is reflected in the intensity of the signal which was transmitted from a coupler functioning as a transmitter to a coupler functioning as a receiver by way of the coupling concerned.

For the electrical and/or electromagnetic coupling for the contactless transmission of the at least one electrical and/or electromagnetic signal a sufficiently small distance is initially required, as the physical interaction processes relevant for the respective coupling in each case become weaker with increasing distance. The coupling thus preferably takes place via a distance dimension between the first transmission unit and the second transmission unit, which is smaller by several orders of magnitude than the dimensions of the device. However in a range of distances of this kind, minor variations in the distance between the first transmission unit and the second transmission unit, as may easily arise as a result of the relative movement of the first device part with reference to the second device part and of the play in the case of this relative movement, can lead to significant relative variations in the distance.

Here, the physical interaction processes relevant for the respective coupling can however have a functional dependence on the distance, which does not necessarily lead to a monotonic rise in the coupling strength as the distance diminishes, but can also have more complex functional dependences, for example as a result of destructive interferences affecting wave components of the signal and the nontrivial distance dependence of interferences of this kind.

Through the arrangement of a first auxiliary coupler in the first transmission unit, whose dimensions differ significantly from those of the first coupler within the framework of the relevant length scales, an additional coupling can now be provided with the second coupler for the transmission of the signal. Within the framework of the anticipated variations in distance resulting from the relative movement of the first device part with reference to the second device part, this additional coupling can be designed in such a way that the functional distance dependence of the coupling strength differs significantly from the functional distance dependence of the coupling strength between the first coupler and the second coupler. In particular the coupling between the first auxiliary coupler and the second coupler for such distances in each case has a value close to a local maximum, for which the coupling strength between the first coupler and the second coupler in each case has a value close to the local minimum. Thus for distances in which a destructive interference is present in the case of one of the two couplings, a constructive interference is preferably present in the other coupling.

Despite the variation in distance and the thus fluctuating coupling strengths it can therefore always be made possible for at least one of the two couplings, that is via the first coupler or via the first auxiliary coupler to the second coupler, to be used for the transmission of the signal.

In at least one embodiment, the transmission here takes place in particular in such a way that the first coupler and the first auxiliary coupler respectively work as transmitters, and the second auxiliary coupler, acting as a receiver, receives both signals, wherein the two signals are to be separated from each other accordingly for further processing. On the other hand it is also possible to have the second coupler send out a signal as a transmitter, and the first coupler and the first auxiliary coupler receive the signal, wherein the final output signal can be formed from the two received signals by way of overlaying and noise suppression where applicable. The last-mentioned variant is simpler to realize from the technical perspective. Only one transmitter is required for multiple receivers. The quality of the received signal is improved by the overlaying.

It has proved to be advantageous if the first transmission unit and the second transmission unit are set up to transmit the at least one electrical and/or electromagnetic signal via at least one capacitive coupling between the first coupler and/or the first auxiliary coupler on the one hand and the second coupler on the other hand. The first coupler, the first auxiliary coupler and the second coupler are in this case to be embodied as electrodes, wherein the first coupler and the second coupler on the one hand and the first auxiliary coupler and the second coupler on the other hand in each case form a capacitance. To this end, as regards the potentials to be used and the spatial dimensions of the electrodes, the distances in the two capacitances are to be set accordingly. The different functional distance dependences of the two capacitances are preferably achieved via different geometries and/or dimensioning of the electrodes of the first coupler and of the first auxiliary coupler.

For the contactless transmission of electrical and/or electromagnetic signals between a transmitter and a receiver spatially separated from the transmitter, which performs a relative movement with reference to the transmitter, a capacitive coupling is particularly advantageous, if the relative movement essentially takes place transversely to the spacing direction of the first coupler and the first auxiliary coupler relative to the second coupler. Minor variations in the distances between the first coupler and the second coupler or between the first auxiliary coupler and the second coupler, which could in each case lead to a change in the strength of the capacitive coupling, can be balanced out via the respectively different coupling strengths of the first capacitance and the second capacitance. In particular, overdriving of a signal which was transmitted by way of the capacitive coupling in a capacitance can here be balanced out by the remaining capacitance.

The first transmission unit and the second transmission unit are preferably set up to transmit the at least one electrical and/or electromagnetic signal via an optical directional coupling between the first coupler and the second coupler on the one hand and/or the first auxiliary coupler and the second coupler on the other hand. An optical directional coupling should here be taken to mean a coupling in which an optical signal guided by a waveguide, whose modes in some cases propagate outside the waveguide, "crosstalk" to a further waveguide which is parallel to the waveguide at least in sections, and hereby ensure a propagating optical signal there too.

For the contactless transmission of electrical and/or electromagnetic signals between a transmitter and a receiver spatially separated from the transmitter, which performs a relative movement with reference to the transmitter, an optical directional coupling is advantageous if the relative movement essentially passes transversely to the distance direction of the first coupler and of the first auxiliary coupler in relation to the second coupler. Minor variations in the distances between the first coupler and the second coupler or between the first auxiliary coupler and the second coupler, which could in each case lead to a change in the strength of the optical directional coupling, can be balanced out via the respectively different coupling strengths of both waveguides of the first transmission unit with the waveguide of the second transmission unit.

Here, the first coupler, the first auxiliary coupler and the second coupler in each case are preferably embodied as dielectric waveguides, wherein the first coupler and the first auxiliary coupler have significantly different coupling lengths. In the case of the optical directional coupling it is thus possible in this way to achieve in a particularly simple manner the different functional distance dependence of the couplings between the first coupler or respectively the first auxiliary coupler and the second coupler and thus the desired coverage of a large range of possible distances with a coupling strength sufficient for the transmission.

In an advantageous embodiment of the invention the first transmission unit has at least one further auxiliary coupler. In particular applications, variations in distance occur between the first transmission unit and the second transmission unit as a result of the relative movement of the first device part with reference to the second device part, which substantially exceed the length constants relevant for the coupling strength. In such a case in particular the best possible coverage of all distance values which occur in the case of the relative movement can now be achieved by way of sufficient variation in the dimensioning of the first coupler and the auxiliary coupler, with sufficient coupling strength for at least one of the said couplers for the transmission of the signal.

At least one embodiment of the invention further specifies a data-generating device which comprises a first device part, a second device part and a transmission system of the previously described type, wherein the first device part is set up to perform a movement relative to the second device part during operation of the device, and wherein either the first transmission unit or the second transmission unit of the transmission system is arranged on the first device part, and the other transmission unit of the transmission system in each case is arranged on the second device part. The advantages specified for the transmission system and for its developments can be transferred analogously to the data-generating device.

In one advantageous embodiment of the data-generating device, the first device part is set up to perform a rotational movement in relation to an axis fixed by the second device part during operation of the device. For the variations in distance occurring as a result of, and limited by, the rotational movement, which occur between a first transmission unit and a second transmission unit of a transmission system, the proposed embodiment of the first transmission unit and the second transmission unit and the thus proposed type is particularly favorable for the transmission of the signal. In particular a periodicity present in the variations in distance and thus in the coupling strengths as a result of the rotational movement can also be taken into account during the signal processing. If for example the first transmission unit is arranged on the second device part and thus primarily serves to receive data, then—if applicable after prior calibration with the aid of test runs—periodically occurring variations in distance can be used to anticipate the variations in the coupling strength, and for reception, according to the rotation phases, to further use primarily the signal of the first coupler or primarily of the first auxiliary coupler, on a selective basis.

Here, the first transmission unit and the second transmission unit are expediently arranged in an axial direction relative to each other in relation to the axis. An arrangement of this kind, in which the electrical and/or electromagnetic coupling takes place primarily in an axial direction, is in particular then advantageous if depending on the application, the axial play of the first device part resulting from imbalances or the like is smaller than its radial play.

On the other hand it may also be advantageous if the first transmission unit and the second transmission unit are arranged in a radial direction relative to each other in relation to the axis. An arrangement of this kind, in which the electrical and/or electromagnetic coupling takes place primarily in a radial direction, is then in particular advantageous if depending on the application, the radial play of the first device part as a result of imbalances or the like is smaller than its axial play.

The concrete case depends in particular upon the mass distribution within the first device part and further upon whether a fine structure of further components exists within the first device part, which during the rotation on their part complete a relative movement in relation to the rotating first device part, as a result of which imbalances may occur. If such relative movements of components within the first device part take place primarily in an axial direction to the latter, the axial play increases. If the mass distribution diverges significantly from a rotational symmetry, the first device part will always also experience an acceleration with a considerable local radial component upon its rotation. In the case of the arrangement of the first transmission unit and the second transmission unit, factors of this nature are preferably to be taken into account.

In a further advantageous embodiment of the invention, the data-generating device is embodied as a computed tomography device, wherein the first device part is formed by the rotating assembly (gantry) and the second device part is formed by the mounting frame. In the case of computed tomography in particular a substantial amount of image data is generated in a short time as a result of the X-ray exposures, which is to be forwarded directly to the medical image processing facility for the purposes of the application. Because of the high rotational speed of the gantry a contactless transmission should preferably be selected here. The proposed embodiment with the transmission system described, whose first transmission unit has a first coupler and a first auxiliary coupler, is here particularly suitable to transmit image data of ever higher resolution from the gantry to the mounting frame.

At least one embodiment of the invention further specifies a method for the transmission at least of an electrical and/or electromagnetic signal from a first device part of a data-generating device to a second device part of the device, wherein the first device part performs a relative movement with reference to the second device part, and wherein an electrical and/or electromagnetic coupling is created at least temporarily between a first coupler arranged on the first device part and second coupler arranged on the second device part and a first auxiliary coupler arranged on the first device part and the second coupler in each case, or an electrical and/or electromagnetic coupling is created at least temporarily between a first coupler arranged on the second device part and a second coupler arranged on the first device part and a first auxiliary coupler arranged on the second device part and the second coupler in each case. It is here provided for the electrical and/or electromagnetic signal to be transmitted in a first signal transmission phase via the coupling between the first coupler and the second coupler, and to be transmitted in a second signal transmission phase via the coupling between the first auxiliary coupler and the second coupler.

The first signal transmission phase is here formed by a phase in which as a result of the distance between the first coupler and the second coupler, a coupling strength sufficient for the transmission of the signal is present. The second signal transmission phase is here formed by a phase in which as a result of the relative movement of the first device part with reference to the second device part, the distance between the first auxiliary coupler and the second coupler is now such that sufficient coupling strength is present between the two for the transmission of the signal. In particular in the second signal transmission phase, the distance between the first coupler and the second coupler is now such that insufficient coupling strength for the transmission of the signal is present between the two.

Parts and variables which correspond to one another are provided with the same reference numerals in all the figures.

FIG. 1 shows a data-generating device 1 in schematic form in a cross-sectional representation, which is embodied as a CT 2. The CT 2 comprises a first device part 4, which is formed by the gantry 6, and a second device part 8, which is formed by the mounting frame 10. During operation of the CT 2, the gantry 6 performs a rotational movement about the axis 12, which is fixed with reference to the mounting frame 10. The patient couch 14 is here arranged in such a way that a patient if possible lies on the axis 12. Components for the medical imaging, which are not shown in greater detail in FIG. 1, are arranged in the gantry 6. The generated image data is now to be transmitted via the transmission system 16 to the mounting frame 10, from which it is forwarded to an image processing unit, which is not shown in greater detail. The mounting frame 10 has a first transmission unit 18 of the transmission system, while the gantry 6 has a second transmission unit 20 of the transmission system 16.

Figure 2:
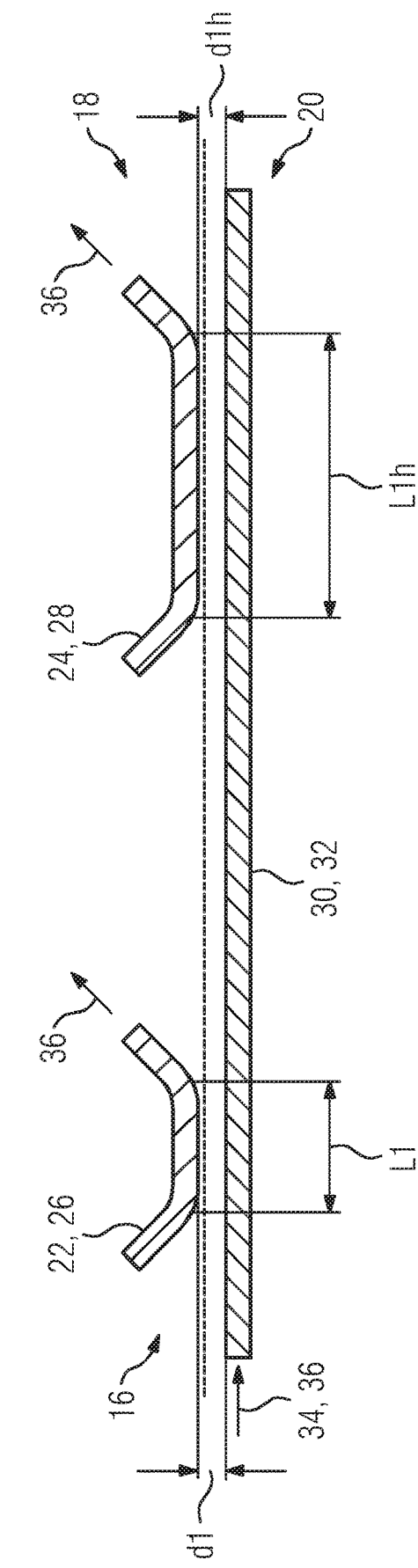
FIG. 2 shows, in an axial sectional representation, the transmission system of the computed tomography device according to FIG. 1.

FIG. 2 shows in schematic form in an axial sectional representation the transmission system 16 according to FIG. 1 for the transmission of the image data from the gantry 6 to the mounting frame 10 in the CT 2. The first transmission unit 18 has a first coupler 22 and a first auxiliary coupler 24. The first coupler 22 and the first auxiliary coupler 24 are in each case embodied as dielectric waveguides 26, 28 with different coupling lengths L1, L1$h$. The second transmission unit 20 has a second coupler 30, which is embodied as a dielectric waveguide 32, which runs on the gantry 6 as an axial ring about the axis 12. The strength of the coupling between the two dielectric waveguides 26 and 32 and the strength of the coupling between the two dielectric waveguides 28 and 32 have a strong, nontrivial functional dependence on the local distance d1, d1$h$ of the respective dielectric waveguides to each other. The distances d1, d1$h$ in some cases vary considerably as a result of the rotation of the gantry 6 and the imbalances and the play, as a result of which the coupling of the wave 34 guided by the second dielectric waveguide 32 into the dielectric waveguide 26 or the dielectric waveguide 28 respectively can vary strongly in its intensity, wherein the concrete distance dependence is here provided in each case by a more complex, non-monotonic function. The coupling lengths L1, L1$h$ are now to be selected in such a way that the respective coupling strengths for different distances are maximized within the framework of the expected distance interval, and that for every distance in the expected distance interval, at least in one of the two dielectric waveguides 26, 28 adequate coupling-in of the wave 34 in which the image data signal 36 to be transmitted is coded, can be achieved.

The aforementioned dependence of the coupling strengths on the distance is indicated in FIG. 3 by a functional graph. The coupling strengths K1 and K1$h$ for the coupling between the first coupler or the first auxiliary coupler respectively and the second coupler are plotted against a distance d. The two coupling strengths K1, K1$h$ here display non-monotonic behavior. Although in the expected distance interval id, that is the range within which the distance d1 or d1$h$ between the first coupler or the first auxiliary coupler respectively and the second coupler would vary in each case during operation of the CT, at least one of the two coupling strengths K1, K1$h$ lies above the limit value Kcrit sufficient for the transmission of the data, while this would not be the case for the coupling strengths K1, K1$h$ isolated from each other.

Although the invention has been more closely illustrated and described in detail by way of the preferred example embodiment, the invention is not limited by this example embodiment. Other variations can be derived by the person skilled in the art, without departing from the protective scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. A transmission system for contactless transmission of at least one of an electrical and electromagnetic signal from a first device part of a data-generating device to a second device part of the device via at least one of electrical and electromagnetic coupling, wherein the first device part is set up to perform movement relative to the second device part during operation of the device, the transmission system comprising:
   a first transmission unit including a first coupler and a first auxiliary coupler, the first auxiliary coupler being of a size different than the first coupler; and
   a second transmission unit including a second coupler, either the first transmission unit or the second transmission unit being arranged on the first device part and the other of the first or the second transmission unit being arranged on the second device part, wherein respective coupling strengths between the first coupler and the second coupler and between the first auxiliary coupler and the second coupler, for the at least one of electrical and electromagnetic coupling, have respectively different functional distance dependences.

2. The transmission system of claim 1, wherein the first transmission unit and the second transmission unit are set up to transmit the at least one of electrical and electromagnetic signal via at least one capacitive coupling between at least one of the first coupler and the first auxiliary coupler on the one hand and the second coupler on the other hand.

3. The transmission system of claim 2, wherein the first transmission unit includes at least one further auxiliary coupler.

4. The transmission system of claim 1, wherein the first transmission unit and the second transmission unit are set up to transmit the at least one of electrical and electromagnetic signal via an optical directional coupling between at least one of the first coupler and the second coupler on the one hand and between the first auxiliary coupler and the second coupler on the other hand.

5. The transmission system of claim 4, wherein the first coupler, the first auxiliary coupler and the second coupler are each respectively embodied as dielectric waveguides, and wherein the first coupler and the first auxiliary coupler have significantly different coupling lengths.

6. The transmission system of claim 5, wherein the first transmission unit includes at least one further auxiliary coupler.

7. The transmission system of claim 4, wherein the first transmission unit includes at least one further auxiliary coupler.

8. The transmission system of claim 1, wherein the first transmission unit includes at least one further auxiliary coupler.

9. The transmission system of claim 1, wherein dimensions of the first coupler differ from those of the first auxiliary coupler within a framework of relevant length scale.

10. The transmission system of claim 1, wherein the first coupler and the first auxiliary coupler are transmitters/receivers.

11. A data-generating device, comprising
   a first device part and a second device part, wherein the first device part is set up to perform a movement relative to the second device part during operation of the device; and
   a transmission system including
      a first transmission unit including a first coupler and a first auxiliary coupler, the first auxiliary coupler being of a size different than the first coupler, and
      a second transmission unit including a second coupler, either the first transmission unit or the second transmission unit being arranged on the first device part and the other of the first or the second transmission unit being arranged on the second device part, wherein respective coupling strengths between the first coupler and the second coupler and between the first auxiliary coupler and the second coupler, for at least one of electrical and electromagnetic coupling, have respectively different functional distance dependences,
   wherein one of the first transmission unit or the second transmission unit of the transmission system is arranged on the first device part, and the other of the first transmission unit and the second transmission unit of the transmission system is arranged on the second device part.

12. The data-generating device of claim 11, wherein the first device part is set up to perform a rotational movement in relation to an axis fixed by the second device part during operation of the data-generating device.

13. The data-generating device of claim 12, wherein the first transmission unit and the second transmission unit are arranged in an axial direction relative to the axis.

14. The data-generating device of claim 13, wherein the data-generating device is embodied as a computed tomography device and wherein the first device part is formed by a rotating assembly of the computed tomography device and the second device part is formed by a mounting frame of the computed tomography device.

15. The data-generating device of claim 12, wherein the first transmission unit and the second transmission unit are arranged in a radial direction relative to the axis.

16. The data-generating device of claim 15, wherein the data-generating device is embodied as a computed tomography device and wherein the first device part is formed by a rotating assembly of the computed tomography device and the second device part is formed by a mounting frame of the computed tomography device.

17. The data-generating device of claim 12, wherein the data-generating device is embodied as a computed tomography device and wherein the first device part is formed by a rotating assembly of the computed tomography device and the second device part is formed by a mounting frame of the computed tomography device.

18. A method for transmission of at least one of electrical and electromagnetic signal from a first device part of a data-generating device to a second device part of the device, the first device part being configured to perform a relative movement with reference to the second device part, the method comprising:

provifing a first coupler of a first size and a second coupler of a size different from the first size;

at least temporarily creating at least one of electrical and electromagnetic coupling between the first coupler arranged on the first device part and the second coupler arranged on the second device part and between a first auxiliary coupler arranged on the first device part and the second coupler, or at least temporarily creating at least one of electrical and electromagnetic coupling between the first coupler arranged on the second device part and the second coupler arranged on the first device part and between the first auxiliary coupler arranged on the second device part and the second coupler; and transmitting the at least one of electrical and electromagnetic signal in a first signal transmission phase via the coupling between the first coupler and the second coupler, and transmitting the at least one of electrical and electromagnetic signal in a second signal transmission phase via the coupling between the first auxiliary coupler and the second coupler.

19. The method of claim 18, further comprising, prior to the transmitting, setting up a first transmission unit and a second transmission unit to transmit the at least one of electrical and electromagnetic signal via at least one capacitive coupling between at least one of the first coupler and the first auxiliary coupler on the one hand and the second coupler on the other hand.

20. The method of claim 18, further comprising, prior to the transmitting, setting up a first transmission unit and a second transmission unit to transmit the at least one of electrical and electromagnetic signal via an optical directional coupling between at least one of the first coupler and the second coupler on the one hand and between the first auxiliary coupler and the second coupler on the other hand.

21. The method of claim 20, wherein the first coupler, the first auxiliary coupler and the second coupler are each respectively embodied as dielectric waveguides, and wherein the first coupler and the first auxiliary coupler have significantly different coupling lengths.

22. The method of claim 20, wherein the first transmission unit includes at least one further auxiliary coupler.

* * * * *